United States Patent [19]

Engelhardt et al.

[11] Patent Number: 5,792,880
[45] Date of Patent: Aug. 11, 1998

US005792880A

[54] PROCESS FOR THE PREPARATION OF N-LAUROYL-L-GLUTAMIC ACID DI-N-BUTYLAMIDE

[75] Inventors: Fritz Engelhardt, Chesapeake, Va.; Manfred Müller, Gelnhausen, Germany; Michael Wessling, Charlotte, N.C.

[73] Assignee: Hoechst Aktiengesellschaft, Frankfurt, Germany

[21] Appl. No.: 816,599

[22] Filed: Mar. 13, 1997

[30] Foreign Application Priority Data

Mar. 15, 1996 [DE] Germany ............ 196 10 323.1

[51] Int. Cl.$^6$ .................................................. C07C 231/00
[52] U.S. Cl. ........................ 554/57; 554/35; 554/51; 554/56

[58] Field of Search .................... 554/57, 35, 51, 554/56

[56] References Cited

PUBLICATIONS

CA 105(15):153544s (1986) (corresponds to JP 61 00050 A2).

*Primary Examiner*—Paul J. Killos
*Attorney, Agent, or Firm*—Miles B. Dearth

[57] ABSTRACT

The present Application relates to a process for the preparation of N-lauroyl-L-glutamic acid di-n-butylamide by reaction of N-lauroyl-L-glutamic acid dimethyl ester with n-butylamine in the presence of a hydrocarbon or hydrocarbon mixture as an auxiliary solvent.

7 Claims, No Drawings

PROCESS FOR THE PREPARATION OF N-LAUROYL-L-GLUTAMIC ACID DI-N-BUTYLAMIDE

DESCRIPTION

The present Application relates to a process for the preparation of N-lauroyl-L-glutamic acid di-n-butylamide by reaction of N-lauroyl-L-glutamic acid dimethyl ester with n-butylamine in the presence of a hydrocarbon or hydrocarbon mixture as an auxiliary solvent.

N-Lauroyl-L-glutamic acid di-n-butylamide is widely described in the patent literature as a thickening agent for mostly hydrophobic, non-polar media. The compound is thus described as an excellent thickener for the production of pressure-sensitive paper, of photosensitive printing plates, of "solid fuel" based on butane and of vulcanization products, for thickening photographic developer waste solutions, and for various cosmetic uses, for example lipsticks.

However, the properties of the product which are classified as very beneficial for these uses prove to be an extreme hindrance during its preparation. This particularly applies to a process procedure which is acceptable from an ecological/economic standpoint, which should, where possible, lead to good yields of a product of high purity without producing relatively large quantities of waste and waste water.

There are a large number of synthesis routes adequately cited in the literature for the preparation of carboxylic and dicarboxylic acid diamides. Depending on the reactivity and the individual case in question, the most diverse carboxylic acid derivatives can be used as starting substances, such as, for example, carboxylic acid chlorides, anhydrides or esters or also other carboxylic acid amides. The variant via the acid chloride, which is as a rule most promising in respect of conversion and yield, does not apply in the present case, since N-lauroyl-L-glutamic acid dichloride is accessible only with difficulty. Direct condensation of carboxylic acids with amines as a rule requires more drastic conditions, such as, for example, higher temperature and operation under increased pressure. The preparation of N-lauroyl-L-glutamic acid di-n-butylamide by direct condensation is described in CA 105(17), 153544s (1986) (corresponds to JP 61 00050 A2). However, the Applicant's own experiments gave yields of only between 40 and 60% in this reaction, the product as a rule still comprising relatively large quantities of impurities.

The reaction of carboxylic acid esters with amines is usually carried out in an inert solvent or in the alcohol of the ester as the solvent. An excess of amine is usually used here, in order to render the conversion as complete as possible. If the desired product cannot be crystallized and recrystallized easily, it is isolated via aqueous working up, as a rule large amounts of amine- and alcohol-containing waste waters being obtained. Experience shows that this involves extensive working up steps.

The reaction of N-lauroyl-L-glutamic acid dimethyl ester with n-butylamine is extremely difficult, working up after the actual reaction being particularly burdened with problems. In particular, in very many inert solvents, such as, for example, aromatics, such as toluene, but also in glycols, ethers and the like, N-lauroyl-L-glutamic acid di-n-butylamide tends to form a gel and to include impurities, in particular of n-butylamine, which indeed, as mentioned, must be employed in excess. The solvents mentioned therefore cannot be used. In practice, no suitable solvents for recrystallization of the product for the purpose of purification can be discovered, because of the properties mentioned.

If aqueous working up after the reaction has been carried out is therefore chosen, a substantially butylamine-free product of acceptable purity and yield is obtained only with great expense and with the production of large amounts of waste water which, in addition to various organic impurities, comprise the butylamine excess employed in the synthesis and the methanol liberated during formation of the amide.

There is therefore an urgent need for a synthesis route for N-lauroyl-L-glutamic acid di-n-butylamide which does not have the disadvantages described above. Surprisingly, it has now been found that a very pure N-lauroyl-L-glutamic acid di-n-butylamide which is practically free from butylamine is accessible in good yields and without any production of waste water starting from N-lauroyl-L-glutamic acid dimethyl ester if the reaction is carried out in the presence of a hydrocarbon or a hydrocarbon mixture as an auxiliary solvent. Simple conversion of the diester into the diamide with reaction-promoting, partial removal of the methanol liberated, and problem-free working up and isolation of the product are possible by this route.

The present invention therefore relates to a process for the preparation of N-lauroyl-L-glutamic acid di-n-butylamide by reaction of N-lauroyl-L-glutamic acid dimethyl ester with n-butylamine, which comprises carrying out the reaction in the presence of a hydrocarbon or a hydrocarbon mixture as an auxiliary solvent.

The n-butylamine is expediently employed in excess, based on N-lauroyl-L-glutamic acid dimethyl ester. 2.1 to 10 mol of amine are preferably employed per mole of ester, particularly preferably 3 to 6 mol of amine per mole of ester. In this manner, the n-butylamine simultaneously functions as a solvent.

The hydrocarbons or hydrocarbon mixtures employed as an auxiliary solvent preferably have boiling points above 60° C., particularly preferably above 100° C. Examples of suitable hydrocarbons are n-nonane, n-decane, n-undecane, n-dodecane and polyalkylated cyclohexane derivatives having boiling points above 100° C., such as, for example, trimethylcyclohexane, methylethylcyclohexane and diethylcyclohexane.

Suitable hydrocarbon mixtures are, in particular, mixtures of the above-mentioned hydrocarbons, in particular high-boiling cyclohexane derivatives. Such mixtures are known to the expert and are commercially available.

The hydrocarbons or hydrocarbon mixtures are preferably employed in amounts of 20 to 300% by weight, particularly preferably in amounts of 50 to 150% by weight, based on the N-lauroyl-L-glutamic acid dimethyl ester.

When the reactants have reacted, the product is worked up and isolated. In a preferred embodiment of the process according to the invention, this is done by first removing excess n-butylamine by distillation and then precipitating the product by addition of a polar solvent.

Suitable polar solvents are, in particular, alcohols, ethers, esters and alkanones, for example acetone.

If a hydrocarbon or a hydrocarbon mixture with a sufficiently high boiling point, in particular above 100° C., is chosen for the reaction, the n-butylamine (boiling point 77.8° C.) can be recovered via a column in this manner and if appropriate re-used.

Even after removal of the n-butylamine, the reaction mixture can still be handled and does not pass through too high a viscosity.

To precipitate the product, an amount of the polar solvent such that it is precipitated completely and in a form which can be filtered is advantageously used. After the precipitation, the product is filtered off and, if desired, can be washed with further solvent. The contents of impurities, which are in themselves already low, can be further reduced by these rinsings. As a rule, the purity of the product obtained by the process according to the invention is >95%, typically even >97%.

The N-lauroyl-L-glutamic acid dimethyl ester required as a starting substance is a compound which is known from the literature and can be prepared by processes known to the expert.

EXAMPLE 1

In a 1 l Quickfit flask with a glass-jacketed thermosensor, gas inlet, stainless steel anchor stirrer and heatable (67°–70° C.) pre-column with an attached Claisen bridge and subsequent cold trap, 110 g of N-lauroyl-L-glutamic acid dimethyl ester (LGA-DME) and 100 g of a mixture of cyclohexane derivatives (trimethylcyclohexane, methylethylcyclohexane and diethylcyclohexane in an approximate ratio of 45:25:10) are initially introduced under a gentle stream of $N_2$. 110 g of n-butylamine are metered in over a period of 30 minutes and the mixture is heated under reflux. During the reaction, portions of the methanol liberated during the amidation are separated off, with a little n-butylamine, via the temperature-controlled pre-column. After refluxing for about 8 hours, monitoring by TLC indicates quantitative conversion. The excess n-butylamine is distilled off, first under normal pressure and then in vacuo, and the product is precipitated by addition of acetone. The precipitate formed is filtered off with suction, washed with acetone, dried and comminuted. The target product N-lauroyl-L-glutamic acid di-n-butylamide is obtained in a good yield of about 80% and in excellent purity (LGB 99% (HPLC), nBuNH$_2$ 50 ppm (GC), other impurities <1%) in the form of a colorless powder of melting point 150°–152° C.

COMPARISON EXAMPLE

In a 1 l Quickfit flask with a glass-jacketed thermosensor, gas inlet, stainless steel anchor stirrer and reflux condenser, 110 g of N-lauroyl-L-glutamic acid dimethyl ester (LGA-DME) in 20 g of MeOH are initially introduced under a gentle stream of $N_2$. 110 g of n-butylamine are metered in over a period of 30 minutes and the mixture is heated under reflux for 8 hours. The reaction mixture is dissolved in 100 g of methanol and 400 g of water are metered into the solution, the product precipitating in gelatinous form. To achieve the abovementioned values for residual butylamine, working up is carried out as follows:

The dough-like precipitate obtained is filtered off with suction, stirred into 300 g of 1N HCl, washed twice with 250 g of water to pH 3, stirred into 2×300 g of 1N NaOH and subsequently washed with approximately 2000 g of water until the filtrate gives a neutral reaction.

The resulting dough-like paste is dried and comminuted. The target product N-lauroyl-L-glutamic acid di-n-butylamide is obtained in a yield of about 70% and in moderate purity (LGB 78% (HPLC), n-BuNH$_2$ 180 ppm (GC), lauric acid butylamide 5% (HPLC), other impurities >15%) in the form of a largely colorless powder of melting range 135°–145° C. The large amounts of waste water obtained must be worked up.

We claim:

1. A process for the preparation of N-lauroyl-L-glutamic acid di-n-butylamide by reaction of N-lauroyl-L-glutamic acid dimethyl ester with n-butylamine, which comprises carrying out the reaction in the presence of a non-aromnatic hydrocarbon or a non-aromatic hydrocarbon mixture as an auxiliary solvent.

2. The process as claimed in claim 1, wherein 3 to 6 mol of n-butylamine are employed per mole of N-lauroyl-L-glutamic acid dimethyl ester.

3. The process as claimed in claim 1, wherein a hydrocarbon or hydrocarbon mixture having a boiling point above 100° C. is employed.

4. The process as claimed in claim 1, wherein n-nonane, n-decane, n-undecane, n-dodecane or a polyalkylated cyclohexane derivative having boiling points above 100° C. are employed as the hydrocarbon or hydrocarbon mixture.

5. The process as claimed in claim 1, wherein the hydrocarbon or hydrocarbon mixture is employed in amounts of 50 to 150% by weight, based on the N-lauroyl-L-glutamic acid dimethyl ester.

6. The process as claimed in claim 1, wherein, after the reaction has taken place, excess n-butylamine is removed by distillation and N-lauroyl-L-glutamic acid di-n-butylamide is then precipitated by addition of a polar solvent or solvent mixture.

7. The process as claimed in claim 6, wherein acetone is employed for the precipitation of the N-lauroyl-L-glutamic acid di-n-butylamide.

* * * * *